United States Patent [19]
Chu et al.

[11] Patent Number: 5,618,813
[45] Date of Patent: Apr. 8, 1997

[54] BENZO[5.6]PYRANO[2.3.4-IJ]QUINOLIZINE AND BENZO[5.6]THIOPYRANO[2.3.4-IJ]QUINOLIZINE DERIVATIVES AS ANTIBACTERIAL AND ANTINEOPLASTIC AGENTS

[75] Inventors: Daniel T. Chu, Santa Clara, Calif.; Qun Li, Gurnee; Kathleen Raye, Highland Park, both of Ill.

[73] Assignee: Abbott Laboratories, Abbott Park, Ill.

[21] Appl. No.: 451,243

[22] Filed: May 26, 1995

[51] Int. Cl.$^6$ .................. A61K 31/535; A61K 31/495; A61K 31/44; C07D 491/147
[52] U.S. Cl. .................. 514/233.2; 514/254; 514/288; 544/125; 544/361; 546/66
[58] Field of Search .................. 546/66, 243; 514/288, 514/229.5, 254, 233.2; 544/125, 361

[56] References Cited

U.S. PATENT DOCUMENTS

| | | | |
|---|---|---|---|
| 4,528,285 | 7/1985 | Chu | 514/224 |
| 4,607,032 | 8/1986 | Chu | 514/212 |
| 5,318,965 | 6/1994 | Chu | 514/229.5 |

FOREIGN PATENT DOCUMENTS

| | | |
|---|---|---|
| 9116894 | 11/1991 | WIPO. |
| 9510519 | 4/1995 | WIPO. |

*Primary Examiner*—C. Warren Ivy
*Assistant Examiner*—Evelyn Huang
*Attorney, Agent, or Firm*—Mona Anand

[57] ABSTRACT

Benzo[5.6]pyrano[2.3.4-ij]quinolizine and benzo[5.6]thiopyrano[2.3.4-ij]quinolizine compounds having the formula

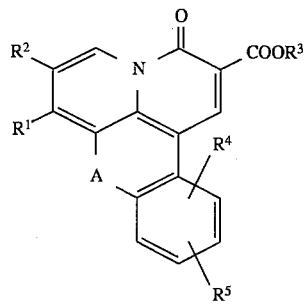

wherein A is sulfur or oxygen; $R^1$ is selected from the group consisting of hydroxy, protected-hydroxy, $C_1$–$C_6$-alkoxy, halo, amino, $C_1$–$C_6$-alkylamino, hydroxy-$C_1$–$C_6$-alkylamino, bicyclic nitrogen-containing heterocycle, nitrogen-containing aromatic heterocycle, and nitrogen-containing heterocycle; $R^2$ is selected from the group consisting of hydrogen, halo, $C_1$–$C_6$-alkyl, or halo-$C_1$–$C_6$-alkyl; $R^3$ is selected from the group consisting of hydrogen, $C_1$–$C_6$-alkyl or $C_5$–$C_7$-cycloalkyl; and $R^4$ and $R^5$ are independently selected from the group consisting of hydrogen, $C_1$–$C_6$-alkyl or $C_1$–$C_6$-alkoxyl, having utility as intermediates or having antibacterial or antineoplastic activity

16 Claims, No Drawings

BENZO[5.6]PYRANO[2.3.4-IJ]QUINOLIZINE AND BENZO[5.6]THIOPYRANO[2.3.4-IJ]-QUINOLIZINE DERIVATIVES AS ANTIBACTERIAL AND ANTINEOPLASTIC AGENTS

TECHNICAL FIELD

This invention relates to novel compounds that are derivatives of benzo[5.6]pyrano[2.3.4-ij]quinolizine and benzo[5.6]thiopyrano[2.3.4-ij]quinolizine. These compounds have been found to possess antibacterial and antineoplastic activity. The invention further relates to pharmaceutical preparations containing these compounds, and to the use of such preparations for treatment of bacterial and neoplastic diseases in mammals.

BACKGROUND OF THE INVENTION

It is known that certain quinolone compounds possess antibacterial activities. For example, D. Chu, U.S. Pat. No. 4,607,032, has disclosed 1-substituted-amino-2-fluoro-4-oxo-4H-quino[2,3,4-i,j][1,4]benzoxazine-5-carboxylic acid derivatives which possess antibacterial activity. Closely related quinobenzothiazine and quinobenzoxazine derivatives having antibacterial activity have also been disclosed by Chu in U.S. Pat. Nos. 4,528,285, 4,529,725, and 4,542,133. Certain quinobenzoxazine derivative having antineoplastic activities have been disclosed by Chu in U.S. Pat. No. 5,318,965. It is also known that certain quinolizinone compounds possess antibacterial activities. These compounds, for example, have been disclosed by Chu in PCT application No. WO91/16894, published Nov. 14, 1991.

SUMMARY OF THE INVENTION

The compounds of the present invention are represented by the following structural formula (I):

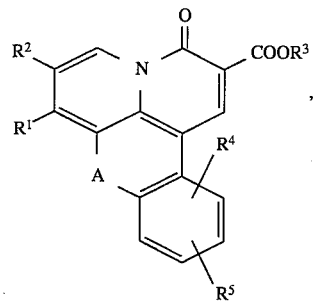

or a pharmaceutically acceptable salt, ester or amide thereof, wherein:

A is sulfur or, preferably, oxygen;
$R^1$ is selected from the group consisting of:
(a) hydroxy;
(b) protected-hydroxy, as defined below;
(c) $C_1$–$C_6$-alkoxy, as defined below;
(d) halo, as defined below;
(e) amino;
(f) $C_1$–$C_6$-alkylamino, as defined below;
(g) hydroxy-$C_1$–$C_6$-alkylamino, as defined below;
(h) bicyclic nitrogen-containing heterocycle, as defined below;
(i) nitrogen-containing aromatic heterocycle, as defined below;
and
(j) nitrogen-containing heterocycle, as defined below;
$R^2$ is selected from the group consisting of hydrogen, halo, $C_1$–$C_6$-alkyl, as defined below, and halo-$C_1$–$C_6$-alkyl, as defined below;
$R^3$ is selected from the group consisting of hydrogen, carboxy-protecting group, $C_1$–$C_6$-alkyl and $C_5$–$C_7$-cycloalkyl, as defined below; and
$R^4$ and $R^5$ are independently selected from the group consisting of hydrogen, $C_1$–$C_6$-alkyl and $C_1$–$C_6$-alkoxy.

Certain compounds of the present invention have utility in the preparation of pharmacologically active compounds of the invention.

The pharmacologically active compounds of the present invention have antibacterial and antineoplastic activity, and they may be prepared as pharmaceutical compositions useful in the treatment of bacterial or neoplastic infections in humans and other animals.

DETAILED DESCRIPTION AND PREFERRED EMBODIMENTS

The nomenclature of the benzo[5.6]pyrano[2.3.4-ij]quinolizine and benzo[5.6]thiopyrano[2.3.4-ij]quinolizine ring systems of the present invention is based upon the following numbering of the ring atoms:

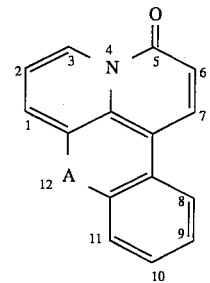

In one embodiment of the invention are compounds of Formula (I) wherein A is oxygen.

In one embodiment of the invention are compounds of Formula (I) wherein A is sulfur.

In a preferred embodiment of the invention are compounds of Formula (I) wherein A is oxygen; $R^1$ is selected from the group consisting of amino, $C_1$–$C_6$alkylamino, hydroxy-$C_1$–$C_6$-alkylamino, bicyclic nitrogen-containing heterocycle, nitrogen-containing aromatic heterocycle, and nitrogen-containing heterocycle; $R^2$ is halo; and $R^4$ and $R^5$ are hydrogen.

The following compounds are representative of the compounds of the invention wherein A of formula (I) is oxygen:
1-(1-morpholinyl)-2-fluoro-5H-5-oxo-benzo[5.6]pyrano[2.3.4-ij]quinolizine-6-carboxylic acid;
1-(3-aminopyrrolidinyl)-2-fluoro-5H-5-oxo-benzo[5.6]pyrano[2.3.4-ij]quinolizine-6-carboxylic acid;
1-(3aα, 4β, 7aα-4-aminooctahydro-[1H]-isoindol-2-yl)-2-fluoro-5H-5-oxo-benzo[5.6]pyrano[2.3.4-ij]quinolizine-6-carboxylic acid;
1-(3-aminomethylpyrrolidinyl)-2-fluoro-5H-5-oxo-benzo[5.6]pyrano[2.3.4-ij]quinolizine-6-carboxylic acid;
1-(3-(ethylaminomethyl)pyrrolidinyl)-2-fluoro-5H-5-oxo-benzo[5.6]pyrano[2.3.4-ij]quinolizine-6-carboxylic acid;
1-(3-(1-amino-1-methylethyl)pyrrolidinyl)-2-fluoro-5H-5-oxo-benzo[5.6]pyrano[2.3.4-ij]quinolizine-6-carboxylic acid;
1-(3-(1--aminoethyl)pyrrolidinyl)-2-fluoro-5H-5-oxo-benzo[5.6]pyrano[2.3.4-ij]quinolizine-6-carboxylic acid;

1-(3-(1-aminocyclopropyl)pyrrolidinyl)-2-fluoro-5H-5-oxo-benzo[5.6]pyrano[2.3.4-ij]quinolizine-6-carboxylic acid;

1-(4-amino-2,3,3a,4,7,7a-hexahydro-[1H]-isoindol-2-yl)-2-fluoro-5H-5-oxobenzo[5.6]pyrano[2.3.4-ij]quinolizine-6-carboxylic acid;

1-(4-amino-2,3,3a,4,5,7a-hexahydro-[1H]-isoindo-2-yl)-2-fluoro-5H-5-oxo-benzo[5.6]pyrano[2.3.4-ij]quinolizine-6-carboxylic acid;

1-(4-amino-2,3,4,5,6,7-hexahydro-[1H]-isoindol-2-yl)-2-fluoro-5H-5-oxo-benzo[5.6]pyrano[2.3.4-ij]quinolizine-6-carboxylic acid;

1-(3-amino-azetidinyl)-2-fluoro-5H-5-oxo-benzo[5.6]pyrano[2.3.4-ij]quinolizine-6-carboxylic acid;

1-(3-(norvalylamino)pyrrolidinyl)-2-fluoro-5H-5-oxo-benzo[5.6]pyrano[2.3.4-ij]quinolizine-6-carboxylic acid;

1-(3-(alanylamino)pyrrolidinyl)-2-fluoro-5H-5-oxo-benzo[5.6]pyrano[2.3.4ij]quinolizine-6-carboxylic acid;

1-(6-amino-3-azabicyclo[3.1.0]hex-3-yl)-2-fluoro-5H-5-oxo-benzo[5.6]pyrano[2.3.4-ij]quinolizine-6-carboxylic acid;

1-(1-amino-5-azaspiro[2.4]hept-5-yl)-2-fluoro-5H-5-oxo-benzo[5.6]pyrano[2.3.4-ij]quinolizine-6-carboxylic acid;

1-(piperazinyl)-2-fluoro-5H-5-oxo-benzo[5.6]pyrano[2.3.4-ij]quinolizine-6-carboxylic acid;

1-(2-methylpiperazinyl)-2-fluoro-5H-5-oxo-benzo[5.6]pyrano[2.3.4-ij]quinolizine-6-carboxylic acid;

1-(4-methylpiperazinyl)-2-fluoro-5H-5-oxo-benzo[5.6]pyrano[2.3.4-ij]quinolizine-6-carboxylic acid;

1-(3-aminopiperidinyl)-2-fluoro-5H-5-oxo-benzo[5.6]pyrano[2.3.4-ij]quinolizine-6-carboxylic acid;

1-(4-aminopiperidinyl)-2-fluoro-5H-5-oxo-benzo[5.6]pyrano[2.3.4-ij]quinolizine-6-carboxylic acid;

1-(3-aminopyrrolidiny)-2-fluoro-5H-9-methyl-5-oxo-benzo[5.6]pyrano[2.3.4ij]quinolizine-6-carboxylic acid;

1-(3-aminopyrrolidiny)-2-fluoro-5H-9-methoxy-5-oxo-benzo[5.6]pyrano[2.3.4ij]quinolizine-6-carboxylic acid;

1-(3-aminopyrrolidiny)-2-fluoro-5H-9,11-dimethyl-5-oxo-benzo[5.6]pyrano[2.3.4ij]quinolizine-6-carboxylic acid; and 1-(3-aminopyrrolidiny)-2-fluoro-5H-9,11 -dimethoxy-5-oxobenzo[5.6]pyrano[2.3.4-ij]quinolizine-6-carboxylic acid.

The following compounds are representative of the compounds of the invention wherein A is sulfur:

1-(1-morpholinyl)-2-fluoro-5H-5-oxo-benzo[5.6]thiapyrano[2.3.4-ij]quinolizine-6-carboxylic acid; and 1-(3-amino-pyrrolidinyl)-2-fluoro-5H-5-oxo-benzo[5.6 ]thiapyrano[2.3.4ij]quinolizine-6-carboxylic acid.

The following compounds are representative of the preferred compounds of the present invention:

1-(1-morpholinyl)-2-fluoro-5H-5-oxo-benzo[5.6]pyrano[2.3.4-ij]quinolizine-6-carboxylic acid;

1-(3-amino-pyrrolidinyl)-2-fluoro-5H-5-oxo-benzo[5.6]pyrano[2.3.4-ij]quinolizine-6-carboxylic acid; and 1-(3aα, 4β, 7aα-4-aminooctahydro-[1H]-isoindol-2-yl)-2-fluoro-5H-5-oxo-benzo[5.6]pyrano[2.3.4-ij]quinolizine-6-carboxylic acid.

In another embodiment of the invention are compounds of Formula (I) wherein A is oxygen or sulfur, and $R^1$ is selected from the group consisting of hydroxy, protected-hydroxy, $C_1$–$C_6$-alkoxy and halo, having utility as intermediates.

The following compounds are representative of the compounds of the invention wherein A is oxygen and $R^1$ is selected from the group consisting of hydroxy, protected-hydroxy, $C_1$–$C_6$-alkoxy and halo:

1-chloro-2-fluoro-5H-5-oxo-benzo[5.6]pyrano[2.3.4-ij]quinolizine-6-carboxylic acid;

1-hydroxy-2-fluoro-5H-5-oxo-benzo[5.6]pyrano[2.3.4-ij]quinolizine-6-carboxylic acid; and 1-t-butyloxy-2-fluoro-5H-5-oxo-benzo[5.6 ]pyrano[2.3.4-ij]quinolizine-6-carboxylic acid.

The following compounds are representative of the compounds of the invention wherein A is sulfur and $R^1$ is selected from the group consisting of hydroxy, protected-hydroxy, $C_1$–$C_6$-alkoxy and halo:

1-chloro-2-fluoro-5H-5-oxo-benzo[5.6]thiopyrano[2.3.4-ij]quinolizine-6-carboxylic acid;

1-hydroxy-2-fluoro-5H-5-oxo-benzo[5.6]thiopyrano[2.3.4-ij]quinolizine-6-carboxylic acid; and 1-t-butyloxy-2-fluoro-5H-5-oxo-benzo[5.6]thiopyrano[2.3.4-ij]quinolizine-6-carboxylic acid.

In another aspect of the invention are pharmacologically active compounds of the present invention in pharmaceutical preparations which comprise one or more of the compounds of the invention formulated together with one or more non-toxic pharmaceutically acceptable carriers.

Yet another aspect of the invention relates to a pharmaceutical preparations containing these compounds, and to the use of such preparations for treatment of bacterial and neoplastic diseases, in mammals comprising administering to a host animal in need of such treatment a therapeutically effective amount of a pharmacologically active compound of the Formula I.

The pharmacologically active compounds of the present invention have antibacterial activity and possess activity against both human and murine tumor cell lines including leukemia, melanoma, and lung, colon and ovarian carcinomas, as well as having activity against some tumor cell lines known to be resistant to Adriamycin (doxorubicin hydrochloride), an antineoplastic agent currently in use.

The terms "$C_1$–$C_6$-alkyl" and "$C_1$–$C_5$-alkyl" refer to alkyl of from 1 to 6 ($C_1$–$C_6$-) or 1 to 5 ($C_1$–$C_5$-) carbons wherein "alkyl" refers to a monovalent radical derived by removal of one hydrogen atom from an unbranched or branched aliphatic hydrocarbon and containing the number of carbon atoms indicated. Examples of $C_1$–$C_6$-alkyl and $C_1$–$C_5$-alkyl include methyl, ethyl, propyl, butyl, t-butyl, pentyl, isopentyl, hexyl (for $C_1$–$C_6$- only), and the like.

The term "$C_1$–$C_6$-alkoxy" refers to an oxygen atom substituted with an alkyl group of the size indicated, as defined above. Examples include methoxy, ethoxy, propoxy and the like.

The term "$C_1$–$C_6$-alkylamino" refers an amino group which has one or two hydrogen atoms replaced by $C_1$–$C_6$-alkyl substituents, as defined above. Examples include methylamino, ethylamino, dimethylamino and the like.

The term "amino-$C_1$–$C_6$-alkyl" refers to a $C_1$–$C_6$-alkyl group, as defined above, in which at least one hydrogen atom is replaced with an amino group. Examples include aminoethyl, aminomethyl and the like.

The term "alpha-amino acid" refers to a single amino acid. The amino acid can be a naturally occurring amino acid, such as valine or glycine, or may be a synthetic alpha-amino acid, such as cyclohexylalanine, for example. The amino acid may be either in the L- or D-configuration or a mixture (racemate) of the two isomers. If not specified, amino acid substituents are optically active and have the L-configuration.

The term "bicyclic nitrogen-containing heterocycle" refers to a monovalent radical derived by removal of one hydrogen atom from a fused or bridged non-aromatic or fused aromatic ring system containing from seven-to-eleven atoms, one ring containing at least one nitrogen atom, which is the atom of attachment, and, optionally, an additional one or two heteroatoms selected from S, O or N. Examples of bicyclic nitrogen-containing heterocycles include 7:6, 7:5, 6:6, 6:5, 6:4, 6:3, 5:5, 5:4 and 5:3 fused ring systems and 3.2.2, 3.2.1, and 3.1.1 bridged ring systems, for example, benzopyrrolidine, octahydroisoindole, and bicyclo[3.2.2]-nonane. The heterocycle may be unsubstituted or substituted, either on a second nitrogen atom or on a carbon atom, with, for example, $C_1$–$C_6$-alkyl, $C_3$–$C_5$-cycloalkyl, $C_3$–$C_6$-cycloalkyl-$C_1$–C-alkyl, $C_3$–$C_5$-spirocycloalkyl, halo-$C_1$–$C_6$-alkyl, hydroxy-$C_1$–$C_6$-alkyl, hydroxy, halo, amino, amino-$C_1$–$C_6$-alkyl, $C_1$–$C_6$-alkylamino, an alpha-amino acid or a polypeptide of from two to five amino acids. An additional $C_1$–$C_6$-alkyl group may be present in addition to the first substituent group.

The terms "$C_3$–$C_5$-cycloalkyl" and "$C_5$–$C_7$-cycloalkyl" refers to a monovalent radical derived by removal of one hydrogen atom from a saturated carbocyclic ring of from 3 to 5 ($C_3$–$C_5$-) or 5 to 7 carbon atoms, respectively.

The term "halo" refers to a chloro (Cl), bromo (Br), or fluoro (F) group.

The term "halo-$C_1$–$C_6$-alkyl" refers to a $C_1$–$C_6$-alkyl group, as defined above, in which at least one hydrogen atom is replaced with a halo group, as defined above. Examples of halo-$C_1$–$C_6$-alkyl include fluoromethyl, chloroethyl, bromopropyl, trifluoromethyl, fluoroethyl and the like.

The term "hydroxy-$C_1$–$C_6$-alkylamino" refers to a $C_1$–$C_6$-alkylamino group, as defined above, in which at least one hydrogen atom of the hydrocarbon is replaced with a hydroxyl group, such as, for example, 2-hydroxyethylamino.

The term "nitrogen-containing aromatic heterocycle" refers to a monovalent radical derived by removal of one hydrogen atom from an aromatic monocyclic ring system having from five to seven ring atoms of which one ring atom is nitrogen and, optionally one or two additional ring atoms independently selected from S, O and N, and with the remaining atoms being carbon. Examples of nitrogen-containing aromatic heterocycles are pyridine, pyrazine, pyrimidine, pyrrole, pyrazole, imidazole, thiazole, oxazole, isooxazole, substituted derivatives thereof, and the like.

The term "nitrogen-containing heterocycle" refers to a monovalent radical derived by removal of one hydrogen atom from a four- to seven-atom non-aromatic ring system containing at least one nitrogen atom, which is the atom of attachment, and, optionally, an additional one or two heteroatoms selected from S, O or N. Examples of nitrogen-containing heterocycles include azetidine, pyrrolidine, piperidine, piperazine, morpholine, thiomorpholine and the like. The heterocyclic group may be unsubstituted or substituted, either on a second nitrogen atom or on a carbon atom, with, for example, $C_1$–$C_6$-alkyl, $C_3$–$C_5$-cycloalkyl, $C_3$–$C_5$-cycloalkyl-$C_1$–$C_6$-alkyl, $C_3$–$C_5$-spirocycloalkyl, halo-$C_1$–$C_6$-alkyl, hydroxy-$C_1$–$C_6$-alkyl, hydroxy, halo, amino, amino-$C_1$–$C_6$-alkyl, $C_1$–$C_6$-alkylamino, an α-amino acid or a polypeptide of from two to five amino acids. An additional $C_1$–$C_6$-alkyl group may be present in addition to the first substituent group.

The term "peptidyl" refers to a group of one or more α-amino acids, as described above, joined by an amide bond.

The term "phenyl" refers to a monovalent radical derived by removal of one hydrogen atom from an unsubstituted benzene ring or from a benzene ring having one to three non-hydrogen substituents independently selected from the group consisting of halo, hydroxy, alkoxy, alkyl, hydroxy-substituted alkyl, amino, (alkyl)amino, aminoalkyl and a nitrogen-containing heterocycle, as for example aziridinyl, pyrrolidinyl and the like.

The term "spirocycloalkyl" refers to a cyclic; attachment to an existing saturated ring system derived by replacement of the two hydrogen atoms on a single carbon atom with a divalent hydrocarbon radical containing from 2 to 5 carbon atoms, thus providing one carbon atom in common to both rings, for example, $C_3$–$C_5$-spirocycloalkyl, having from 3 to 5 carbon atoms in the spiro-attached ring.

The chiral centers of the compounds of the present invention may have either the R, S, or racemic configuration. Methods of resolution of the enantiomeric forms of these compounds are well known to those skilled in the art. For example, J. March provides a thorough discussion of resolution methods in "Advanced Organic Chemistry", John Wiley and Sons, Inc, New York, (1985), which is incorporated herein by reference.

Protecting groups are well known and widely used by those skilled in the art of organic synthesis. Such groups are used to protect a potentially labile group during a specific reaction, with the intent of removing the group at a later time and restoring the functionality of the group being protected.

For example, The term "carboxy-protecting group" refers to and includes the residue of a carboxylic acid ester group. Such carboxy-protecting groups have been extensively used in the protection of carboxyl groups in the penicillin and cephalosporin fields, as described in U.S. Pat. Nos. 3,840,556 and 3,719,667, which are incorporated herein by reference. In general, such carboxy-protecting groups can be relatively easily cleaved to yield the free carboxy group. Representative protecting groups include $C_1$–$C_8$ alkyl (e.g., methyl, ethyl, tertiary, butyl), substituted alkyl (e.g., dimethylaminoethyl), benzyl and substituted derivatives thereof such as alkoxy and nitrobenzyl groups; also suitable are acyl groups such as pivaloyloxymethyl groups.

Additionally, the term "protected-hydroxy" refers to a hydroxy group in which the hydrogen atom has been replaced with a protecting group. In general, such hydroxy-protecting groups may be removed relatively easily to yield the free hydroxy group. Representative protecting groups include substituted esters (e.g., methoxymethyl, tetrahydrofuranyl, benzyl), silyl ethers (e.g., trimethylsilyl), esters (e.g., formate, acetate, trifluoroacetate), carbonates and carbamates.

Similarly, sulfhydryl groups may be protected and deprotected when it is so desired, and such groups include, for example, methoxymethyl and 2-tetrahydropyranyl.

For additional examples of additional protecting groups, see for example, T. H. Greene and P. G. M. Wuts, *Protective Groups in Organic Synthesis*, 2nd edition, John Wiley & Sons, New York (1991), which is incorporated herein by reference).

Amino acid synthesis requires protecting groups also, and many of these are described in "Peptide Synthesis" Second Edition, M. Bodansky, Y. S. Klausner and M. A. Ondetti (1976), which is incorporated herein by reference. As in conventional peptide synthesis, branched chain amino and carboxyl groups at alpha and omega positions in amino acids may be protected and deprotected if necessary.

Examples of protecting groups for amino groups include, for example, benzyloxycarbonyl (Z), o-chlorobenzyloxycarbonyl ((2-Cl)Z)), p-nitrobenzyloxycarbonyl (Z($NO_2$)), p-methoxybenzyloxycarbonyl (Z(OMe)), t-amyloxycarbonyl (Aoc), isobornyloxycarbonyl, adamantyloxycarbonyl (Adoc), 2-(4-biphenyl)-2-propyloxy carbonyl (Bpoc), 9-fluorenyl-methoxycarbonyl (Fmoc), methylsulfonylethoxy carbonyl (Msc), trifluoroacetyl, phthalyl, formyl, 2-nitrophenylsulfonyl (Nps), diphenylphosphinothioyl (Ppt) and dimethylphosphino-thioyl (Mpt).

The examples for protecting groups for carboxyl groups of amino acids include, for example, benzyl ester (OBzl), cyclohexyl ester, 4-nitrobenzyl ester (OBzlNO$_2$), t-butyl ester (OtBu), 4-pyridylmethyl ester (OPic) and the like.

Further, specific amino acids having functional groups other than amino and carboxyl groups in the branched chain such as arginine, cysteine, serine and the like may be protected, if necessary, with suitable protecting groups. It is preferable that, for example, the guanidino group, (NG) in arginine may be protected with nitro, p-toluenesulfonyl (Tos), benzyloxycarbonyl (Z), adamantyloxycarbonyl (Adoc), p-methoxybenzenesulfonyl, 4-methoxy-2,6-dimethyl-benzenesulfonyl (Mts) and the like, and the thiol group in cysteine may be protected with benzyl, p-methoxybenzyl, triphenylbenzyl, acetamidomethyl, ethylcarbamyl, 4-methylbenzyl (4-MeBzl), 2,4,6-tlrimethylbenzyl (Tmb) and the like, and the hydroxy group in serine may be protected with benzyl (Bzl), t-butyl, acetyl, tetrahydropyranyl (THP) and the like.

The term "prodrug" refers to compounds that are rapidly transformed in vivo to yield the parent compound of the above formula, as for example by hydrolysis in blood. T. Higuchi and V. Stella provide a thorough discussion of the prodrug concept in "Pro-drugs as Novel Delivery Systems", Volume 14 of the A. C. S. Symposium Series, which is incorporated herein by reference.

The term "pharmaceutically acceptable salts, esters and amides" refers to those carboxylate salts, amino acid addition salts, esters and amides of the compounds of Formula I as well as the zwitterionic forms thereof, which are, within the scope of sound medical judgment, suitable for use in contact with the o tissues of humans and lower animals without undue toxicity, irritation, allergic response and the like; commensurate with a reasonable benefit/risk ratio; and effective for their intended use.

Examples of pharmaceutically acceptable salts include hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate and laurylsulphonate salts and the like. These salts can be prepared in situ during the final isolation and purification of the compounds or by separately reacting the purified compound in its free base form o with a suitable organic or inorganic acid and isolating the salt thus formed. (See, for example, S. M. Berge, et al., "Pharmaceutical Salts," *J. Pharm. Sci.*, 66:1–19 (1977), which is incorporated herein by reference.)

Examples of pharmaceutically acceptable, non-toxic esters of the compounds of Formula I include C$_1$-to C$_6$-alkyl esters wherein the alkyl group is straight or branched chain. Acceptable esters also include C$_5$- to C$_7$-cycloalkyl esters. C$_1$- to C$_4$-alkyl esters are preferred. Esters of the compounds of Formula I may be prepared according to conventional methods.

Examples of pharmaceutically acceptable, nontoxic amides of the compounds of Formula I include amides derived from ammonia, primary C$_1$- to C$_6$-alkyl amines and secondary C$_1$- to C$_6$- dialkyl amines wherein the alkyl groups are straight or branched chain. In the case of secondary amines, the amine may also be in the form of a 5- or 6-membered heterocycle containing one nitrogen atom. Amides derived from ammonia, C$_1$- to C$_3$- alkyl primary amides of Formula I may be prepared according to conventional methods. It is intended that amides of the present invention include amino acid and peptide derivatives.

The term "neoplastic diseases" refers to disorders and disease states characterized by abnormal proliferative cell growth, such as leukemias, lymphomas, myelomas, melanoma, sarcomas, blastomas and tumors of the head, thyroid, neck, brain, esophagus, lung, breast, stomach, pancreas, genitourinary tract, and the like. Antineoplastic agents are chemical compounds which are effective in the treatment of any one or more neoplastic disease. Chemotherapy of neoplastic diseases is described in "Goodman and Gilman's The Pharmacological Basis of Therapeutics", 8th edition, A. G. Gilman, et al., eds., N.Y., Pergamon Press, (1990).

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

As is well know in the art, these compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, as for example by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as carboxymethylcellulose, alginates, gelatin, polyvinylpyrrolidone, sucrose and acacia, c) humectants such as glycerol, d) disintegrating agents such as agaragar, calcium carbonate, potato or tapioca starch, alginic acid, certain silicates, and sodium carbonate, e) solution retarding agents such as paraffin, f) absorption accelerators such as quaternary ammonium compounds, g) wetting agents such as cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract or, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are well-known in the art. See, for example, Prescott, Ed., *Methods in Cell Biology*, Volume XIV, Academic Press, New York, N.Y. (1976), p. 33 et seq., which is incorporated herein by reference Dosage forms for topical administration of a compound of this invention include powders, sprays, ointments and inhaliants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to, gradually increase the dosage until the desired effect is achieved.

Dosage regimens must be titrated to the particular neoplasm, the condition of the patient and the response obtained, but generally dosage levels o of about 0.1 to about 750 mg/kg body weight, more preferably of about 0.25 to about 500 mg/kg body weight, and most preferably about 0.5 to about 300 mg of active compound per kilogram of body weight per day are administered orally or intravenously to a mammalian patient. If desired, the effective daily dose may be divided into multiple doses for purposes of administration, e.g., two to four separate doses per day.

Schemes

In general, the compounds of the present invention may be prepared according to reaction Schemes 1,2 or 3 below. In these schemes the substituent groups are as defined in connection with Formula 1 above.

Certain abbreviations are used repeatedly in the schemes and examples which follow. These include: BOC for t-butoxycarbonyl; (BOC)2 for di-t-butyl dicarbonate; CBZ for benzyloxy-carbonyl; DMF for dimethyl formamide; DMSO for dimethyl sulfoxide; HRMS for high resolution mass spectroscopy; LAH for lithium aluminum hydride; LDA for lithium diethyl amide; RaNi for Raney Nickel; and THF for tetrahydrofuran.

According to Scheme 1, perfluoropyridine is reacted with an alkali salt of t-butanol, such as for example, sodium t-butoxide or lithium t-butoxide, in a polar organic solvent such as THF, first at from 10° C. to −78° C. for 1–4 hours, then at room temperature for 2–72 hours, to give the compound of formula 2. The compound of formula 2 is then reacted with hydrazine under nitrogen at reflux temperature for 2–8 hours, and after removal of excess hydrazine the compound of formula 3 is dissolved in an organic solvent, such as methanol or benzene, for example, and air is then passed through the solution for 8–16 hours to give the compounds of formula 4. The compound of formula 4 is then condensed with the dianion of o-cresol (or in the case where $R^4$ and $R^5$ are other than hydrogen with the appropriately substituted o-cresol derivatives), which is prepared by reacting cresol first with a basic hydroxyl-reactive compound, such as sodium or potassium hydride, for example, for 0.25 to 1.0 hours at 0° C., then with a strong base, such as t-butyllithium or s-butyllithium, for example, in a polar solvent such as THF or the like for a period of from 0.5 to 3 hours, first at −78° C. then at ambient temperature for 2–16 hr, to give the compound of formula 5. The fused-ring compound of formula 6 is then prepared by heating the compound of formula 5 with a mild base, such as $K_2CO_3$ or Na2CO3, in the presence of a polar solvent such as DMF or the like. The compound of formula 6 is then reacted with a strong base, such as LDA or the like, at −78° C. under a $N_2$ atmosphere, and condensed with diethyl ethoxy-methylenemalonate in the presence of an anhydrous polar solvent, such as THF or the like, firstly at −78° C. then at ambient temperature.

Scheme 1

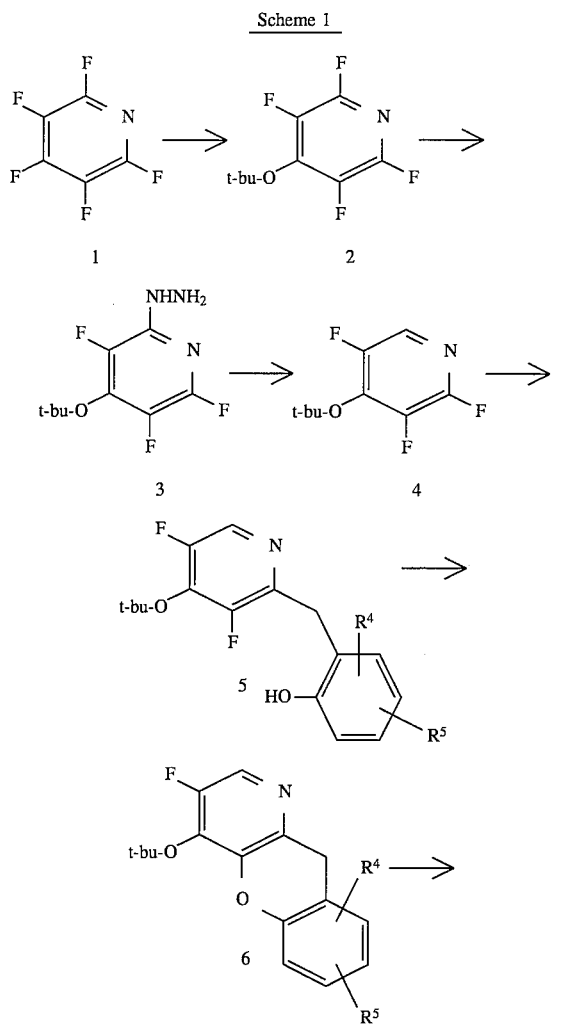

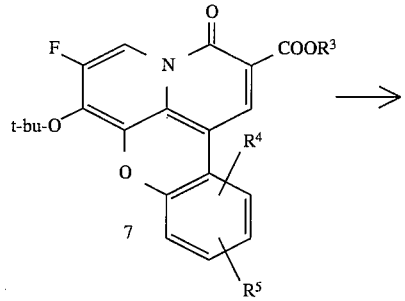

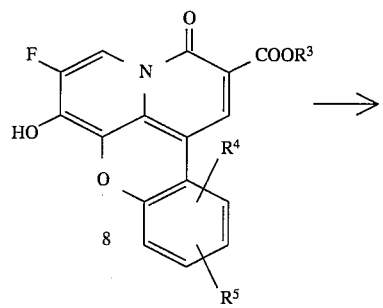

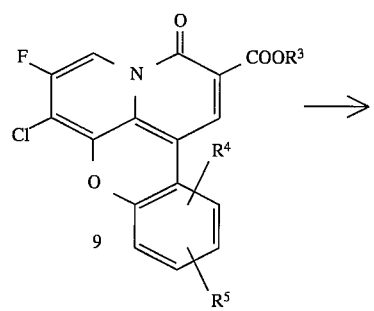

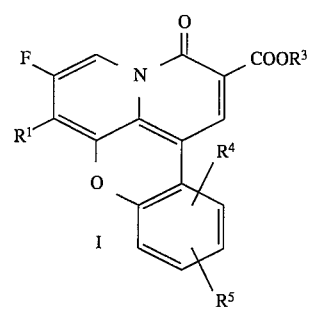

The intermediate product is immediately reacted with a reagent or series of reagents, such as lithium di(trimethylsilyl)amide or DBU (1,8-diaza[5.4.0]undec-7-ene), to decarboxylate the intermediate and close the ring to give the compound of formula 7, wherein R3 is ethyl. The protecting t-butyl group is removed from the compound of formula 7 by hydrolysis with trifluoroacetic acid under nitrogen for 1–8 hours at ambient temperature to give the compound of formula 8. The unprotected material is then reacted with $POCl_3$ in a suitable organic solvent, such as DMF or methylene chloride, for example, at ambient temperature for 8–24 hours in order to prepare the compounds of formula 9. The Cl leaving group in the compounds of formula 9 is then displaced by a nucleophile such as a nucleophilic amine, for example, 3-aminopyrrolidine, or 3aα, 4β, 7aα-4-BOC-amino-octahydro-[1H]-isoindole), to give the corresponding compounds of formula I, wherein $R^1$ is the desired group.

The reaction may be conducted at a temperature from about 20° C. to about 130° C. in a suitable organic solvent such as pyridine, methylene chloride, chloroform or 1-methyl-2-pyrrolidinone. It is desirable to carry out the reaction in the presence of an acid acceptor such as triethylamine, potassium carbonate and the like, at a molar ratio of 1.0 to 2.0 moles of the acid acceptor per mole of compound of the formula 6. The amine can also be used as an acid acceptor in which case two or more equivalents of this reagent are used. The ester may be hydrolyzed by standard methods, such as reaction with lithium hydroxide at reflux for 0.5 to 4 hours, to provide the compound of formula I, wherein $R^3$ is H. If desired a pharmaceutically acceptable salt of I may be prepared by standard methods known to the art.

According to Scheme 2, perfluoropyridine; is reacted with a nucleophilic amine, for example morpholine, to give the compound of formula 10. The reaction may be conducted at a temperature from about 20° C. to about 130° C. in a suitable organic solvent such as pyridine, methylene chloride, chloroform or 1-methyl-2-pyrrolidinone. It is desirable to carry out the reaction in the presence of an acid acceptor such as triethylamine, potassium carbonate and the like, at a molar ratio of 1.0 to 2.0 moles of the acid acceptor per mole of compound of the formula 6. The amine can also be used as an acid acceptor in which case two or more equivalents of this reagent are used. In Scheme 2 it is desirable to select $R^1$ that is stable to all subsequent reactions. By substituting compound 10 for the compound of formula 2 of Scheme 1 and carrying the reaction products forward, the compounds of formulas 11, 12, 13, 14, and 15 are prepared in the manners as described for compounds 3, 4, 5, 6, and 7 of Scheme 1 above. The ester of formula 15 may be hydrolyzed by standard methods, such as reaction with lithium hydroxide at reflux for 0.5 to 4 hours, to provide the compound of formula I, wherein $R^1$ is H. If desired a pharmaceutically acceptable salt of I may be prepared by standard methods known to the art.

Scheme 2

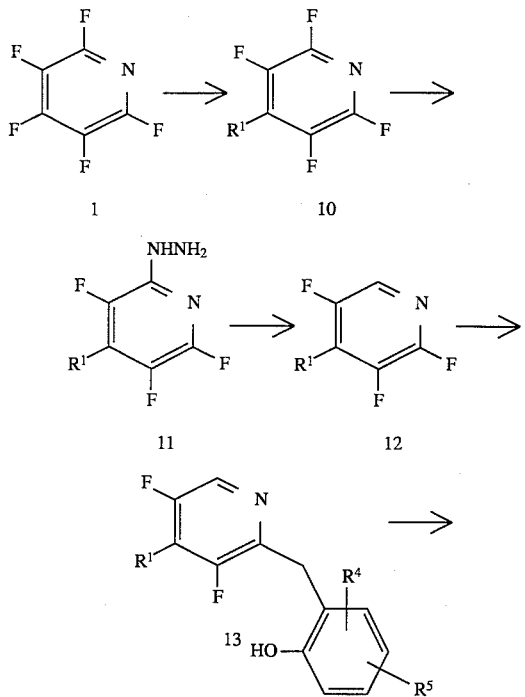

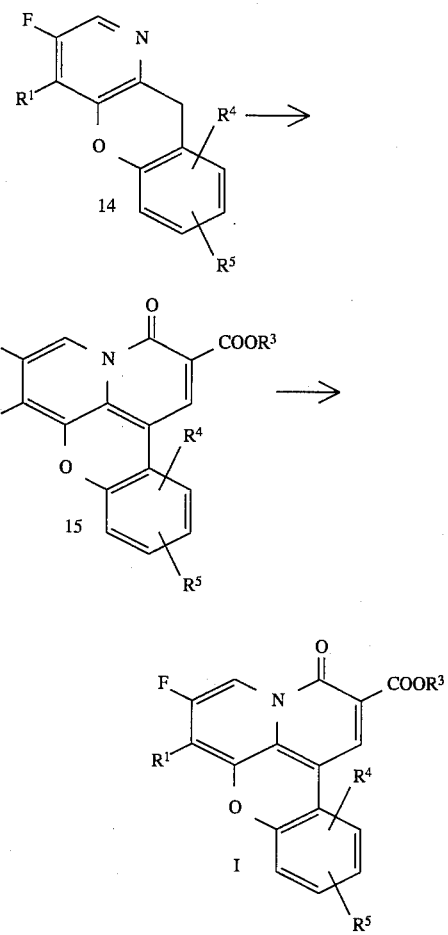

Compounds of Formula (I) where A is sulfur may be prepared according to Scheme 3, wherein the compound (16), wherein X is either a protected hydroxy group as in Scheme 1 or is an $R^1$ group as in Scheme 2, is reacted with an appropriate protected thiocresol, to give the compound (17), wherein Y is a sulfur-protecting group, such as methoxymethyl or 2-tetrahydropyranyl, for example. Compound (17) may then deprotected by treatment with solution of HBr in acetic acid or trifluoroacetic acid, and the deprotected, compound is reacted with a mild base, such as $K_2CO_3$ or $Na_2CO_3$, in the presence of a polar solvent such as DMF or the like to give the compound (18). Compound 18 may then be carried forward in a manner similar to the reactions given for compound (6) in Scheme 1 or compound (14) in Scheme 2 to give the desired product.

Scheme 3

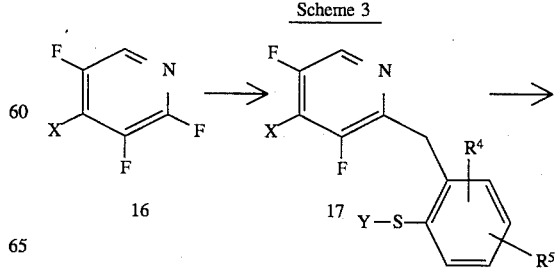

15
-continued
Scheme 3

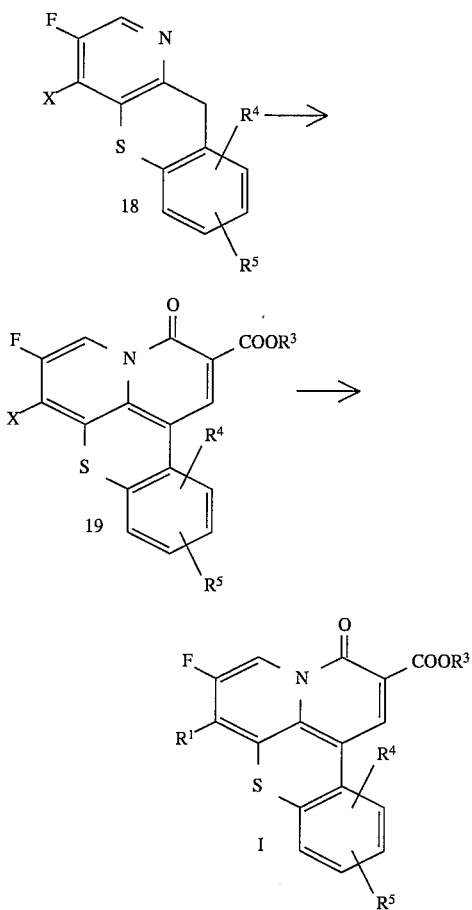

For the preparation of the compounds of Formula I which are alpha-amino acids or peptide derivatives of amine groups in $R^1$, the condensation of the amino group with amino acids and peptides may be effected in accordance with conventional condensation methods such as the azide method, the mixed acid anhydride method, the DCC (dicyclohexylcarbodiimide) method, the active ester method (p-nitrophenyl ester method, N-hydroxysuccinic acid imide ester method, cyanomethyl ester method and the like), the Woodward reagent K method, the DCC-HOBT (1-hydroxybenzotriazole) method and the like. Such reactions are described in "Peptide Synthesis" Second Edition, M. Bodansky, Y. S. Klausner and M. A. Ondetti (1976), which is incorporated herein by reference. It is contemplated that the amino acid coupling reaction could be carried out before or after the amino-containing group is incorporated into the compound by displacement of the 7-fluorine atom of the appropriate intermediate.

The foregoing may be better understood from the following examples, which are presented for the purpose of illustration and not limitation of the scope of the invention.

16
EXAMPLE 1

1-(1-morpholinyl)-2-fluoro-5H-5-oxo-benzo[5.6]-pyrano[2,3.4-ij]quinolizine-6-carboxylic acid 1a. 2,3,5,6-tetrafluoro-4-(1-morpholinyl)pyridine.

A 14.7 g sample of pentafluoropyridine (Aldrich) and 13.24 mL of triethylamine were dissolved in 100 mL of methylene chloride. The solution was cooled to 0° C., and 7.93 mL of morpholine was added slowly. The reaction mixture was stirred at room temperature for 18 hours, then diluted with an equal volume of methylene chloride. The solution was washed with water, 10% HCl, water again, then dried over $MgSO_4$, and evaporated. The residue crystallized upon cooling.

1b. 2.3.5-trifluoro-6-hydrazine-4-(1-morpholinyl)pyridine

A solution of 5.0 g of 2,3,5,6-tetrafluoro-4-(1-morpholinyl)pyridine, from step 1 a above, and 21.4 mL of hydrazine monohydrate in 125 mL of ethanol was heated at reflux for 3 hours. The solvent was removed under vacuum, and the residue was dissolved in methylene chloride. The solution was washed with water, dried over $MgSO_4$, and the solvent was removed to give the title compound, which was taken directly to the next step.

1c. 2.3.5-trifluoro-4-(1-morpholinyl)pyridine

To a suspension of 2,3,5-trifluoro-6-hydrazino-4-(1-morpholinyl)pyridine, from step 1 b above, (7.2 g in 50 mL of water) was added dropwise a solution of 45.5 g of $CUSO_4 \cdot 5 H_2O$ in 200 mL of distilled water. The mixture was stirred for 1 hour at reflux, then cooled and adjusted to pH 9 with conc. $NH_4OH$. This basic mixture was then extracted with ethyl acetate, which was filtered, dried over $MgSO_4$ and concentrated under vacuum. The residue was purified by column chromatography on silica gel, eluting with 1:2 ethyl acetate:hexane to yield 2.88 g of the title compound. $^1H$ NMR ($CDCl_3$) δ: 3.45 (m, 4H), 3.82 (m, 4H), 7.19 (m, 1H).

1d. 3.5-difluoro-2-((2-hydroxyphenyl)methyl)-4-(1-morpholinyl)pyridine

Under anhydrous conditions a solution of 1.0 g of o-cresol in 10 mL of anhydrous THF was added dropwise to a washed and stirred suspension of 1.58 g of 35% KH in 10 mL of anhydrous THF at 0° C. The mixture was stirred under $N_2$ for 15 minutes, then 4.4 mL of n-butyllithium was added. The mixture was stirred for 30 minutes at 0° C., then cooled to −78° C. To this solution was added dropwise a solution of 1.9 g of 2,3,5-trifluoro-4-(1-morpholinyl)pyridine, from step 1 c above, also cooled to −78° C. The reaction mixture was stirred at −78° C. for 20 minutes, then at room temperature for 1.5 hours. The solution was adjusted to pH 9 by addition of satd. $NH_4Cl$ solution, and the mixture was extracted with ether. The extract was washed with brine and water, then dried over $MgSO_4$ and concentrated under vacuum to yield 602 mg of the title compound. MS ($DCI/NH_3$) m/e: 307 $(M+H)^+$. $^1H$ NMR ($CDCl_3$) δ: 3.41 (m, 4H), 3.80 (m, 4H), 4.08 (d, 2H, J=3.0 Hz), 6.83 (m, 1H), 6.96 (d, 1H, J=7.5 Hz), 7.16 (m, 2H), 8.00 (m; 1H).

1e. 3-fluoro-4-(1-morpholinyl)-10H -benzo[5.6]pyrano[3.2-b ][pyridine

A 665 mg sample of 3,5-difluoro-2-((2-hydroxyphenyl)-methyl)-4-(1-morpholinyl)pyridine, from step 1d above, and 360 mg of $K_2CO_3$ were dissolved in 40 mL of anhydrous dimethylacetamide, and the reaction solution was heated at 120° C. for 2 hours. After cooling to room temperature, the reaction was quenched with water, and the mixture was extracted with ether. The extract was dried over $MgSO_4$ and concentrated under vacuum, and the residue was distilled in a kugelrohr apparatus (40° C., 1.7 mm Hg) to remove the solvent. The residual crude product was purified by flash chromatography, eluting with 1:2 ethyl acetate:hexane to yield 620 mg of the title compound. MS (DCI/NH$_3$) m/e: 287 (M+H)$^+$. $^1$H NMR (CDCl$_3$) δ: 3.46 (m, 4H), 3.89 (m, 4H), 4.14 (s, 2H), 7.09 (m, 2H), 8.04 (d, 1H, J=4 Hz).

1f. 2-(3-fluoro-4-(1-morpholinyl)-10H-benzo[5.6]pyrano[3.2.-b][pyridin-10-yl)-ethene-1.1-dicarboxylic acid, diethyl ester A 283 mg sample of 3-fluoro-4-(1-morpholinyl)-10H-benzo[5,6]pyrano[3.2-b][pyridine, from step 1e above, was dissolved in 20 mL of anhydrous THF, and the solution was cooled to −78° C. and maintained under a N$_2$ atmosphere. To this solution was added 0.393 mL of N-butyllithium, and the reaction was stirred for 15 minutes. To this solution was added 0.218 mL of diethyl ethoxymethylenemalonate, and the reaction mixture was stirred at −78° C. for 10 minutes and then at room temperature for 20 minutes. The reaction was quenched by addition of 10% HCl, and the pH was adjusted to about 3. The mixture was extracted with ether, which was dried over MgSO$_4$ and concentrated under vacuum. The crude product was taken directly to the next step.

1g. 1-(1-morpholinyl)-2-fluoro-5H-5-oxo-benzo[5.6]pyrano[2.3.4-ij]quinolizine-6 -carboxylic acid, ethyl ester The crude product from step 1f above was dissolved in 20 mL of absolute ethanol, and 0.12 mL of piperidine and 2 drops of acetic acid were added. The solution was heated at reflux for 18 hours. The solvent was removed, the residue was dissolved in methylene chloride, which was washed with water, then dried over MgSO$_4$ and concentrated under vacuum. The residue was washed with ether, and the product was dried to yield 239 mg of the title compound, which was taken directly to the next step.

1h. 1-(1 -morpholinyl)-2-fluoro-5H-5-oxo-benzo[5,6]pyrano[2.3.4-ij]quinolizine-6-carboxylic acid A 184 mg sample of 1-(1-morpholinyl)-2-fluoro-5H-5-oxo-benzo[2.3.4-ij]quinolizine-6-carboxylic acid, ethyl ester, prepared as in step 1 g above, was dissolved in 11 mL of a 1:2 mixture of water:THF, 37 mg of LiOH·H$_2$O was added, and the mixture was heated at reflux for 1.5 hours. The THF was removed under reduced pressure, and the aqueous residue was made acidic with 1N HCl. The resulting solid was separated by filtration and purified by chromatography on silica gel, eluting with 10% methanol in methylene chloride, to afford 93 mg of the title compound. MS (DCI/NH$_3$) m/e: 383 (M+H)$^+$. $^1$H NMR (CDCl$_3$)δ: 3.58 (m, 4H), 3.91 (m, 4H), 6.97 (m, 1H), 7.20 (m, 2H), 7.66 (m, 1H), 8.50 (s, 1H), 8.77 (d, 1H, J=9 Hz), 13.69 (s, 1H). Anal. calcd. for C$_{20}$H$_{15}$FN$_2$O$_5$·0.5 H$_2$O: C, 61.38; H, 4.12; N, 7.16. Found: C, 61.64; H,3.97; N, 7.05.

EXAMPLE 2

1-(3-amino-pyrrolidinyl)-2-fluoro-5H-5-oxo-benzo[5,6]-pyrano[2.3.4-ij]quinolizine-6-carboxylic acid hydrochloride 2a. 4-t-butoxy-2.3.5.6.,tetrafluoropyridine A 158.5 g (937.6 mmol) sample of pentafluoropyridine (Aldrich) was dissolved in 600 mL of THF and cooled to −78° (To this stirred solution was added a solution of 88.29 g (918.6 mmol) in 80(i mL of THF over a 30 minute period. The reaction mixture was stirred at −78° C. for 30 minutes and at −20° C. for 64 hours. The reaction mixture was diluted with 1.5 L of ether and filtered through diatomaceous earth. The solvent was removed under vacuum, and the residual was distilled under reduced pressure to give 141.34 g of title compound.

2b. 4-t-butoxy-2.3.5-trifluoro-6-hydrazino-pyridine

Following the procedure of example 1 b, substituting the 4-t-butoxy2,3,5,6-tetrafluoropyridine of step 1 a above for the starting material of that example, the title compound was prepared, and taken directly to the next step.

2c. 4-t-butoxy-2.3.5-trifluoropyddine

The product of step 2b above was dissolved in 120 mL of toluene, 60 mL of 20% NaOH solution were added, and air was bubbled through the mixture for 18 hours at room temperature. The mixture was diluted with 100 mL of ether, and the phases were separated. The organic layer was washed, with brine, then water, and dried over MgSO$_4$. The solvent was removed, and the residue was purified by flash chromatography on silica gel, eluting with 1:16 ethyl acetate:hexane to afford 14.6 g of the title compound. $^1$H NMR (CDCl$_3$) δ1.45 (m, 9H), 7.86 (m, 1H).

2d. 4-t-butoxy-3.5-difluoro-2-((2,hydroxyphenyl)methyl)-pyridine

Under anhydrous conditions a solution of 5.53 g of o-cresol in 30 mL of anhydrous THF was added dropwise to a washed and stirred suspension of 8.78 g of 35% KH in 50 mL of anhydrous THF at 0° C. The mixture was stirred at 0° C. under N$_2$ for 10 minutes, then 24.6 mL of n-butyllithium was added. The mixture was stirred for 30 minutes at 0° C., then cooled to −78° C. To this solution was added dropwise a solution of 7.0 g of 4-t-butoxy-2,3,5-trifluoropyridine, from step 2c above, in 50 mL of THF, also cooled to −78° C. The reaction mixture was stirred at −78° C. for 20 minutes, then at room temperature for 3 hours. The reaction was quenched with satd. NH$_4$Cl solution, and the mixture was extracted with ether. The solvent was washed with water and dried over MgSO$_4$. The solvent was removed, and the excess o-cresol was removed by heating at 80° C. at 0.25 mm Hg. The crude product was purified by flash chromatography on silica gel, eluting with 1:8 ethyl acetate:hexane, to yield 4.91 g of the title product. MS (DCI/NH$_3$) m/e: 294 (M+H)$^+$. $^1$H NMR (CDCl$_3$) δ: 1.42 (m, 9H), 4.12 (d, J=2.5 Hz, 1 H), 6.83 (m, 1H), 6.97 (m, 1H), 7.17 (m,).H), 8.18 (m, 1H), 10.15 (s, 1H).

2e. 3-fluoro-4-t-butoxy-10H-benzo[5.6]pyrano[3.2:b][pyridine

A 4.91 g sample of 4-t-butoxy-3,5-difluoro-2-((2-hydroxyphenyl)methyl)-pyridine, from step 2d above, and 2.77 g of K$_2$CO$_3$ were dissolved in of anhydrous DMF, and the reaction solution was heated at 120° C. for 24 hours. After cooling to room temperature, the DMF was removed in a kugelrohr apparatus, and the residue was dissolved in ether. The solution was washed with water, dried over MgSO$_4$, and the solvent was removed. The crude product was purified by flash chromatography on silica gel, eluting with 1:8 ethyl acetate:hexane, to yield 2.21 g of the title product. MS (DCI/NH$_3$) m/e: 274 (M+H)$^+$. $^1$H NMR (CDCl$_3$) δ: 1.48 (d, J=l Hz, 9H), 4.18 (s, 2H), 7.10 (m, 2H), 7.23 (m, 2H), 8.17 (d, J=1 Hz, 1H).

2f. 2-(4t-butoxy-3-fluoro-10H-benzo[5,6]pyrano[3.2-b ][pyridin-10-yl)-ethene-1.1-dicarboxylic acid, diethyl ester A 2.21 g sample of 3-fluoro-4-t-butoxy-10H-benzo[5,6] pyrano[3.2-b][pyridine, from step 2e above, was dissolved in 20 mL of anhydrous THF, and the solution was cooled to −78° C. and maintained under a N$_2$ atmosphere. To this solution was added 9.97 mL of a 1.0 M LDA solution, and the reaction mixture was stirred for 30 minutes. Next was added 1.96 mL of diethyl ethoxymethylenemalonate, and the reaction mixture was stirred at −78° C. for 10 minutes and then at room temperature for 1 hour. To assist the reaction, 1 eq of 1 M lithium bis(trimethylsilyl)amide was added at 0° C., and the reaction was stirred at room temperature for 1 hour. The reaction was quenched by addition of satd. NH$_4$Cl solution, and the mixture was diluted with ethyl acetate. The phases were separated, and the organic layer was washed with brine, dried over MgSO$_4$. The solvent was removed to yield a red liquid which was taken directly to the next step.

2g. 1-t-butoxy-2-fluoro-5H-5-oxo-benzo[5.6]pyrano[2.3.4-ij]-quinolizine-6-carboxylic acid, ethyl ester The red liquid from the previous step was dissolved in 30 mL of absolute ethanol, 1.33 mL of 1,8-diazabicyclo[5.4.0]undec-7-ene was added, and the mixture was heated at reflux under N$_2$ for 3 hours. The solvent was removed under vacuum, and the residue was dissolved in methylene chloride. The solution was washed with 1 N HCl, water anti dried over MgSO$_4$. The solvent was removed, and the residue was purified by column chromatography on silica gel, eluting with 1:4 ethyl acetate: methylene chloride, to give 761 mg of title compound, which was taken directly to the next step.

2h. 1-hydroxy-2-fluoro-5H-5-oxo-benzo[5,6]pyrano[2.3.4-ij]quinolizine-6-carboxylic acid, ethyl ester The 761 mg of the compound from step 2g above was dissolved in 10 mL of TFA, and stirred at room temperature under N$_2$ for 15 minutes. The solvent was removed under vacuum, and the; residue was collected (418 mg). MS (DCI/NH$_3$) m/e: 342 (M+H)$^+$. $^1$H NMR (DMSO-d$_6$) δ: 1.30 (t, J=7 Hz, 3Hi, 4.24 (q, J=7 Hz, 2H), 7.03 (m, 1H), 7.15 (m, 2H), 7.68 (m, 1H), 8.20 (s, 1H), 8.83 (d, J=7 Hz, 1H).

2i. 1chloro-2-fluoro-5H-5-oxo-benzo[5.6]pyrano[2.3.4-ij]quinolizine-6-carboxylic acid, ethyl ester A 418 mg sample of the compound from step 2h above was suspended in 15 mL of anhydrous methylene chloride and 0.948 mL of DMF was added. To this reaction mixture was added 1.14 mL of POCl$_3$, and the reaction was stirred at room temperature under N$_2$ for 2 hours. The reaction was quenched with ice and water, then diluted with methylene chloride. The organic layer was washed with brine and water, then dried over MgSO$_4$. The solvent was removed, and the residue was purified by flash chromatography on silica gel, eluting with 2% methanol in methylene chloride to afford 377.8 mg of the title compound. MS (DCI/NH$_3$) m/e: 360 (M+H)$^+$. $^1$H NMR (CDCl$_3$) δ: 1.46 (t, J=7 Hz, 3H), 4.47 (q, J=7 Hz, 2H), 7.16–7.22 (m, 3H), 7.65 (m, 1H), 8.64 (s, 1H), 8.83 (d, J=6 Hz, 1H).

2j. 1-(3-BOC-aminopyrrolidinyl)-2-fluoro-5H-5-oxo-benzo[5.6]pyrano[2.3.4-ij]quinelizine-6-carboxylic acid, ethyl ester A 175 mg sample of 1-chloro-2-fluoro-5H-5-oxo-benzo[5.6]pyrano[2.3.4-ij]quinolizine-6-carboxylic acid, ethyl ester, from step 2i above, was dissolved in 10 mL of acetonitrile, and 271 mg of 3-BOC-aminopyrrolidine and 327 mg of NaHCO3 were added. The reaction mixture was heated at reflux for 18 hours, and the solvent was removed under vacuum. The residue was dissolved in methylene chloride, which was washed with water, then brine and dried over MgSO$_4$. The solvent was removed, and the residue was taken directly to the next step.

2k. 1-(3-BOC-aminopyrrolidinyl)-2-fluoro-5H-5-oxo-benzo[5,6]pyrano[2.3.4-ij]quinolizine-6-carboxylic acid.

A sample of the crude material from the previous step was dissolved in 10 mL of THF, and 163 mg of LiOH·H$_2$O was added. The mixture was heated at reflux under N$_2$ for 2 hours. The reaction mixture was neutralized with 1 N HCl, and the precipitate was collected by filtration. The filtrate was extracted with methylene chloride, which was dried over MgSO$_4$. The solvent was removed, and the residue was combined with the material previously collect. The combined sample was purified by flash chromatography on silica gel, eluting with 100:5:1 methylene chloride:methanol:acetic acid to afford the title compound, which was taken directly to the next step.

2l. 1-(3-aminopyrrolidinyl)-2-fluoro-5H-5-oxo-benzo[5.6]pyrano[2.3.4-ij]quinolizine-6-carboxylic acid hydrochloride The BOC-protected compound from the previous step was dissolved in 2 mL of methylene chloride, then stirred with a small amount of 4 N HCl in dioxane for 2 hours at room temperature. The solution was diluted with ether, and the product was collected by filtration. The solid was washed with methylene chloride, and ether, then dissolved in water and filtered through sintered glass. The solution was freeze-dried to afford 80 mg of the title compound. MS (DCI/NH$_3$) m/e: 382 (M+H)$^+$. $^1$H NMR (DMSO-d$_6$) δ: 2.29 (m, 2H), 3.85–4.16 (m, 5H), 7.13 (m, 2H), 7.27 (m, 1H), 7.51 (m, 1H), 7.69 (m, 1H), 8.38 (s, 1H), 8.86 (d, J=10 Hz, 1H). Anal. calcd. for C$_{20}$H$_{16}$FN$_3$O$_4$·2 HCl·.2 H2O: C, 48.99; H, 4.52; N, 8.57. Found: C, 48.72; H, 4.37; N, 9.15.

EXAMPLE 3

1-(3aα, 4β, 7aα-4-aminooctahydro-[1H]-isoindol-2-yl)-2-fluoro-5H-5-oxo-benzo[5.6]pyrano[2.3.4-ij]quinolizine-6-carboxylic acid hydrochloride 3a. 3aα. 4β, 7aα-4-BOC-amino-octahydro-[1H]-isoindole Two mL of 1.0 N trifluoracetic acid was added to a stirred solution of 2.0 mL of cyclohexane and 4.92 g of N-benzyl-N-(methoxymethyl)trimethylsilylmethylamine (prepared according to Chem. *Pharm. Bull.*, 33:2762 (1985)) in 20 mL of methylene chloride at 0° C. The mixture was stirred at room temperature for 16 hr, then diluted with methylene chloride. The solution was washed with NaHCO$_3$ and water, then dried over MgSO$_4$. Removal of the solvent left an oily residue. The residue was .dissolved in 65 mL of methanol, after which were added 2.2 g of NH$_2$OH.HCl, 10 mL of 10% NaOH, and 6.5 mL of methylene chloride, and the reaction was heated at 60° C. for 3 hr. The solvents were removed, and the residue was dissolved in methylene chloride, which was washed with water, dried over MgSO$_4$ and concentrated to give an oil. The oil was dissolved in 50 mL of THF, 1.57 g of LAH were added, and the mixture was heated at reflux for 2 hr. The reaction was quenched with water, the solid was removed, and the filtrate was concentrated. The concentrate was dissolved in 40 mL of methanol and 10 mL of water. To this solution was added 5.0 g of di-t-butyl dicarbonate and the reaction was stirred for 16 hr. The methanol was removed under vacuum, and the residue was extracted with methylene chloride. The extract was washed with water, dried over MgSO$_4$ and concentrated to give an oil. The oil was purified by chromatography on silica gel, eluting with 100:5:0.5 methylene chloride:methanol:NH$_4$OH to give 0.36 g of the 3aα,4β,7aα isomer and 2.22 g of the 3aα,4α,7aα somer of the title compound. The 3aα,4aβ,7aαisomer was stirred with 0.66 g of 10% Pd/C in 150 mL of methanol under 4 Atm of H$_2$ for 48 hr. The catalyst was filtered off, and the solvent was removed to give the title compound (1.6 g).

3b. 1-(3aα, 4β, 7aα-4-aminooctahydro-[1H]-isoindol-2-yl)-2-fluoro-5H-5-oxo-benzo[5.6]pyrano[2.3.4-ij]quinolizine-6-carboxylic acid hydrochloride A 351 mg (1.46 mmol) sample of 3aα, 4β, 7aα-4-BOC-amino-octahydro-[1H]-isoindole, from step 3a above, and 175 mg (0.486 mmol) of 1-chloro-2-fluoro-5H-5-oxo-benzo[5.6]pyrano[2.3.4-ij]quinolizine-6-carboxylic acid, ethyl ester, from Example 2 step i above, were dissolved in 10 mL of acetonitrile and heated at reflux under N$_2$ for 18 hours. The solvent was removed under vacuum. The residue was dissolved in methylene chloride, which was washed with water and brine, then dried over MgSO$_4$. The solvent was removed and the residue was carried forward as in Example 2, steps j–l, to afford 97 mg of the title compound. MS (DCI/NH₃) m/e: 436 (M-Cl)⁺. ¹H NMR (DMSO-d₆) δ: 1.26–1.37 (m, 2H), 1.63 (m, 2H), 1.82 (m, 2H), 2.28–2.38 (m, 2H), 3.50 (m, 1H), 3.66 (m 3.74–3.90 (m, 1H), 4.18 (m, 2H), 7.14 (m, 1H), 7.21 (m, 1H), 7.32 (m, 1H), 7.68 (m, 1H), 8.12, 8.16 (two s, 1H), 8.70, 8.76 (two d, J=6 Hz, 1H).

EXAMPLES 4–21

Following the procedures of Example 2, steps, j, k and l, above, replacing the 3-BOC-aminopyrrolidine of step 2j with the appropriate unprotected or BOC-protected reagent, the compounds of Examples 4–21 as shown in Table 1 below are prepared.

TABLE 1

Examples 4–21

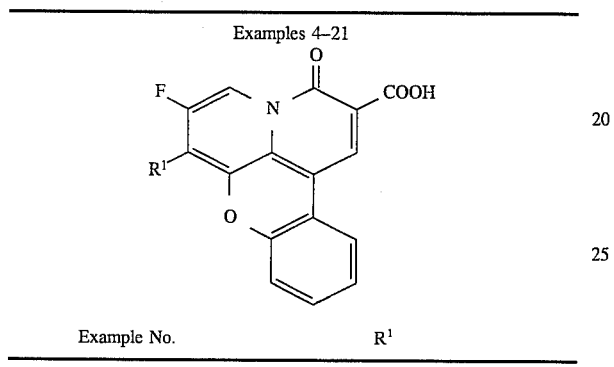

| Example No. | R¹ |
|---|---|
| 4 | H₂N—CH₂—[pyrrolidinyl] |
| 5 | Et-NH-CH₂—[pyrrolidinyl] |
| 6 | H₂N-C(CH₃)₂—[pyrrolidinyl] |
| 7 | H₂N-CH(CH₃)—[pyrrolidinyl] |
| 8 | H₂N-[cyclopropyl]—[pyrrolidinyl] |
| 9 | 4-amino-cyclohexenyl-fused pyrrolidine (NH₂) |
| 10 | 4-amino-cyclohexenyl-fused pyrrolidine (NH₂) |
| 11 | 4-amino-cyclohexyl-fused pyrrolidine (NH₂) |

TABLE 1-continued

Examples 4–21

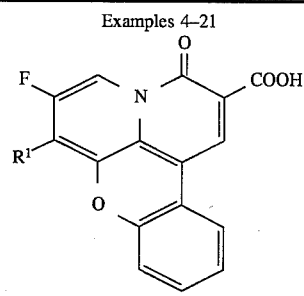

| Example No. | R¹ |
|---|---|
| 12 | H₂N-[azetidinyl]-N— |
| 13 | Norvalyl-NH-[pyrrolidinyl] |
| 14 | alanyl-NH-[pyrrolidinyl] |
| 15 | H₂N-[bicyclo cyclopropyl-pyrrolidinyl] |
| 16 | H₂N-cyclopropyl-CH₂-[pyrrolidinyl] |
| 17 | HN-[piperazinyl]-N— |
| 18 | HN-CH₂-CH(CH₃)-[piperazinyl] |
| 19 | H₃C-N(CH₃)-[piperazinyl] |
| 20 | H₂N-[piperidinyl]-N— |
| 21 | H₂N-[piperidin-4-yl]-N— |

EXAMPLES 22–25

Following the procedures of Example 2, steps d–l above, replacing the o-cresol of step 2d with the substituted o-cresol indicated below, the compounds of Examples 22–25 are prepared as shown in Table 2 below.

TABLE 2

Examples 22–25

| Example No. | starting cresol | substitution of final product |
|---|---|---|
| 22 | HO-C6H2(CH3)(CH3) (2-methyl, 4-methyl) | 9-methyl- ($R^4$ = H, $R^5$ = methyl) |
| 23 | HO-C6H2(CH3)(OCH3) (2-methyl, 4-methoxy) | 9-methoxy- ($R^4$ = H, $R^5$ = methoxy) |
| 24 | HO-C6H(CH3)(H3C)(CH3) (2-methyl, 3-methyl, 5-methyl) | 9,11-dimethyl- ($R^4$ = $R^5$ = methyl) |
| 25 | HO-C6H(CH3)(H3CO)(OCH3) (2-methyl, 3-methoxy, 5-methoxy) | 9,11-dimethoxy- ($R^4$ = $R^5$ = methoxy) |

EXAMPLE 26

1-(1-morpholinyl)-2-fluoro-5H-5-oxo-benzo[5.6]-thiapyrano[2.3.4-ij]quinolizine-6-carboxylic acid Following the procedures of Example 1, except substituting S-methoxymethyl-thiocresol for the cresol of step 1d and isolating the protected intermediate, then removing the protecting group by treatment with HBr in trifluoroacetic acid, then carrying the product forward as in steps 1e–h, the title compound is obtained.

EXAMPLE 27

1-(3-amino-pyrrolidinyl)-2-fluoro-5H-5-oxo-benzo[5.6]thiapyrano[2.3.4-ij]quinolizine-6-carboxylic acid Following the procedures of Example 2, except substituting S-methoxymethyl-thiocresol for the cresol of step 1d and isolating the protected intermediate, then removing the protecting group by treatment with HBr in trifluoroacetic acid, then carrying the product forward as in steps 1e–h, the title compound is obtained.

EXAMPLE 28

Assay of In Vitro Cytotoxicity

The in vitro activity of the compounds of the present invention was demonstrated using a three day microtiter assay to measure the metabolic activity of cultured cells exposed to a range of cytotoxic drug concentrations. Metabolic activity was measured by the cells' ability to reduce the tetrazolium dye, 3-(4,5-dimethylthiazol-2-yl)-2,5-diphenyltetrazolium bromide (MTT), to a quantifiable colored formasan derivative. Surviving cells reduce the MTT dye. The inhibitory concentrations of killing 50% of the cells ($IC_{50}$s) were calculated. Testing was in accord with the following protocol:

Test compounds and a reference antineoplastic agent, Adriamycin™ (doxorubicin hydrochloride), were dissolved in dimethyl sulfoxide (DMSO) and diluted, first with Earle's Balanced Salt Solution (Sigma), followed by culture medium, to twice the highest concentration of the compound to be tested. From this concentrated stock, two-fold serial dilutions were prepared in 96-well microtiter trays, each well containing twice the desired final concentration of the compound. Each concentration was tested in triplicate and compared to triplicate drug-free controls.

The cells were grown in the same medium used for diluting the compounds. Adherent cells were harvested by trypsinization according to the following procedure:

1. Removing the medium by aspiration..
2. Rinsing the cell monolayer twice with Earle's Balanced Salt Solution.
3. Adding trypsin (0.05%)/EDTA (0.53 mM), using approximately 0.2 mL of solution for each 25 $cm^2$; tilting to cover the monolayer, then withdrawing trypsin leaving only a thin film of solution; incubating at room temperature until cell monolayers detach.
4. When the cells have detached as determined by visual and/or microscopic observation, adding medium containing fetal calf serum to stop the action of the trypsin and resuspend the cells; triturating to aid dissociation of cell clumps.
5. Determining the number of cells per milliliter by electronic cell counter (e.g. Coulter Counter) or by mixing an aliquot of cell suspension with Trypan Blue (0.4% in normal saline;) and counting the viable cells using a hemacytometer.

After harvesting by trypsinization, viable cell counts were determined and cell density was adjusted to 25,000 cells/mL. Inoculum (0.1 mL) was then added to each well for a final concentration of 2,500 cells per well. Addition of the inoculum was used to dilute the test compounds to the desired concentration.

Microtiter trays were incubated for three days at 36° C. in a humidified atmosphere containing 5% carbon dioxide.

After three days, 20 microliters of 5 mg/mL MTT in phosphate-buffered solution were added to each well of the microtiter trays. The microtiter trays were then returned to the incubator for two to four hours to allow the surviving cells to reduce the dye. After this incubation, both the medium and the unreduced dye were removed by aspiration. DMSO was added to each well to dissolve the water-insoluble, colored end product of the dye reduction for spectrophotometric measurement at 570 nm.

The results obtained which clearly show the cytotoxicity of the compounds of Examples 1,2 and 3 against human and murine tumor cell lines A549, HT-29, B16F10 and P388, are illustrated in Table 3. (A549 is a human lung cancer cell line; HT-29 is a human colon cancer cell line; B16F10 is a mouse melanoma; and P388 is a animal-passaged mouse leukemia cell line.)

TABLE 3

In Vitro Cytotoxicity ($IC_{50}$) Against Selected Tumor Cell Lines

| Test Compound from Example[a] | Cell Line A549 | Cell Line HT-29 | Cell Line B16F10 | Cell Line P388 |
|---|---|---|---|---|
| 1 | 0.41 | 0.47 | 0.23 | 0.16 |
| 2 | 0.12 | 0.24 | 0.017 | 0.016 |
| 3 | 0.19 | 0.19 | 0.069 | 0.055 |
| ADR[a] | 0.031 | 0.106 | 0.0014 | 0.0033 |

[a] = ADR represents Adriamycin ™ (doxorubicin hydrochloride).

EXAMPLE 29

In Vitro Assay of Antibacterial Activity

The in vitro antibacterial activity of the compounds of the present invention was demonstrated as follows: Minimum inhibitory concentrations (MICs) were determined by the agar dilution method, in which twelve petri dishes were prepared, each containing successive aqueous 2-fold dilutions of the test compounds mixed with 10 mL of sterilized Brain Heart Infusion (BHI) agar (Sigma). Each plate was inoculated with 1:100 (or 1:10 for slow-growing strains, primarily Micrococcus and Streptococcus) dilutions of up to 32 different microorganisms, using a Steers replicator block calibrated to deliver approximately $10^4$ colony forming units (CFUs). The inoculated plates were incubated at from about 35° C. to about 37° C. for approximately 20–24 hours. In o addition, a control plate using BHI agar containing no test compound was prepared and incubated at the beginning and at the end of each test. The quinolone antibacterial ciprofloxacin was used as a control ("Cntl").

After incubation, each petri dish was observed for the presence or absence of microorganism growth. The MIC was defined as the lowest concentration of test compound yielding no growth (a slight haze or sparsely isolated colonies at the inoculum spot) as compared to the growth control containing no test compound.

The results of the above tests, shown in Table 4 below, demonstrate that the compounds of the present invention possess activity against bacterial growth.

TABLE 4

In Vitro Antibacterial Activity (MIC Values in µg/mL)

| Organisms | Cmpd. of Ex. 1 | Cmpd. of Ex. 2 | Cmpd. of Ex. 3 | Ciprofloxacin |
|---|---|---|---|---|
| *Staph. aureus* ATCC 6538P | 0.78 | 6.2 | 0.78 | 0.2 |
| *Staph. aureus* A5177 | 0.78 | 6.2 | 0.78 | 0.39 |
| *Staph. aureus* 5278 | 0.78 | 6.2 | 0.78 | 0.39 |
| *Staph. aureus* 642A | 0.78 | 6.2 | 0.78 | 0.39 |
| *Staph. aureus* NCTC10649 | 0.39 | 3.1 | 0.78 | 0.39 |
| *Staph. aureus* CMX 553 | 0.78 | 6.2 | 0.78 | 0.78 |
| *Staph. aureus* 1775 Cipro.R. | 1.56 | 6.2 | 3.1 | >100 |
| *Staph. epidermidis* 3519 | 0.39 | 3.1 | 0.78 | 0.39 |
| *Entero. faecium* ATCC 8043 | 25 | 6.2 | 1.56 | 0.39 |
| *Strep. bovis* A5169 | 25 | 3.1 | 0.39 | 1.56 |
| *Strep. agalactiae* CMX 508 | 3.1 | 3.1 | 0.39 | 0.39 |
| *Strep. pyogenes* EES61 | 3.1 | 3.1 | 0.39 | 0.78 |
| *Strep. pyogenes* 930 CONST | 6.2 | 3.1 | 0.2 | 0.78 |
| *Strep. pyogenes* 2458 INDUC | 6.2 | 3.1 | 0.39 | 0.39 |
| *M. luteus* ATCC 9341 | 1.56 | 3.1 | 0.39 | 1.56 |
| *M. luteus* ATCC 4698 | 0.39 | 3.1 | 0.78 | 0.78 |
| *Escherichia coli* Juhl | >100 | 3.1 | 6.2 | 0.01 |
| *E. coli* SS | 0.39 | 0.78 | 0.78 | 0.005 |
| *E. coli* DC-2 | >100 | 12.5 | 100 | 0.2 |
| *E. coli* H560 | >100 | 3.1 | 6.2 | 0.01 |
| *E. coli* KNK 437 | 50 | 3.1 | 25 | 0.2 |
| *Enter. aerogenes* ATCC 13048 | >100 | 6.2 | 25 | 0.02 |
| *Klebsiella pneumoniae* ATCC 8045 | 12.5 | 1.56 | 1.56 | 0.02 |
| *Providencia stuartii* CMX 640 | >100 | >100 | 100 | 0.78 |
| *P. aeruginosa* BMH 10 | >100 | 25 | 100 | 0.1 |
| *P. aeruginosa* A5007 | >100 | 100 | >100 | 0.1 |
| *P. aeruginosa* K799/WT | >100 | 50 | >100 | 0.1 |
| *P. aeruginosa* K799/61 | 12.5 | 6.2 | 1.56 | 0.02 |
| *Pseudomonas cepacia* 2961 | 100 | >100 | >100 | 3.1 |
| *Acinetobacter calcoaceticus* CMX 669 | 1.56 | 6.2 | 12.5 | 0.39 |
| *P. aeruginosa* 5263 | >100 | >100 | >100 | 12.5 |
| *P. aeruginosa* 2862 | >100 | >100 | >100 | 12.5 |
| *Candida albicans* CCH 442 | — | >100 | >100 | >100 |
| *Myco. smegmatis* ATCC 114 | — | 3.1 | 0.78 | 0.78 |
| *Nocardia asteroides* ATCC 9970 | — | 3.1 | 1.56 | 12.5 |

It is to be understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of formula

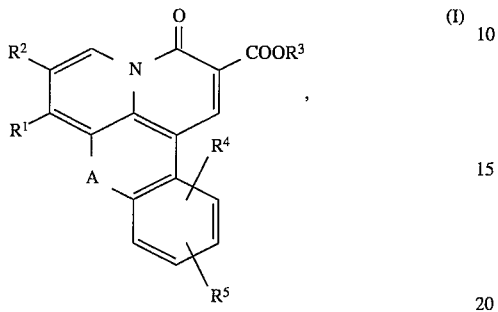

(I)

or a pharmaceutically acceptable salt, ester or amide thereof, wherein:

A is sulfur or oxygen;

$R^1$ is selected from the group consisting of hydroxy, protected-hydroxy, $C_1$–$C_6$-alkoxy, halo, amino, $C_1$–$C_6$-alkylamino, hydroxy-$C_1$–$C_6$-alkylamino, bicyclic nitrogen-containing heterocycle selected from the group consisting of benzopyrrolidine, octahydroisoindole, bicyclo(3,2,2,7-nonane and azabicyclo[3.1.0]hex, nitrogen-containing aromatic heterocycle selected from the group consisting of pyridine, pyrazine, pyrimidine, pyrrole, pyrazole, imidazole, thiazole, oxazole, isooxazole, and nitrogen-containing heterocycle selected from the group consisting of azetidine, pyrrolidine, piperidine, piperazine, morpholine, and thiomorpholine;

$R^2$ is selected from the group consisting of hydrogen, halo, $C_1$–$C_6$-alkyl, and halo-$C_1$–$C_6$-alkyl;

$R^3$ is selected from the group consisting of hydrogen, carboxy-protecting group, $C_1$–$C_6$-alkyl and $C_5$–$C_7$-cycloalkyl; and $R^4$ and $R^5$ are independently selected from the group consisting of hydrogen, $C_1$–$C_6$-alkyl and $C_1$–$C_6$-alkoxy.

2. A compound according to claim 1 wherein A is oxygen.

3. A compound according to claim 2 wherein $R^1$ is selected from the group consisting of amino, $C_1$–$C_6$-alkylamino, hydroxy-.$C_1$–$C_6$-alkylamino, bicyclic nitrogen-containing heterocycle selected from the group consisting of benzopyrrolidine, octahydroisoindole, bicyclo[3.2.2 ]-nonane and azabicyclo[3.1.0]hex, nitrogen containing aromatic heterocycle selected from the group consisting of pyridine, pyrazine, pyrimidine, pyrrole, pyrazole, imidazole, thiazole, oxazole, isoxazole and nitrogen-containing heterocycle selected from the group consisting of azaspiro[2.4]hept, azetidine, pyrrolidine, piperidine, piperazine, morpholine, and thiomorpholine; $R^2$ is halo; and $R^4$ and $R^5$ are hydrogen.

4. A compound according to claim 3 which is:

1-(1-morpholinyl)-2-fluoro-5H-5-oxo-benzo[5.6]pyrano[2.3.4-ij]quinolizine-6-carboxylic acid;

1-(3-aminopyrrolidinyl)-2-fluoro-5H-5-oxo-benzo[5.6]pyrano[2.3.4-ij]-quinolizine-6-carboxylic acid;

1-(3aα, 4α, 7aα-4-aminooctahydro-[1H]-isoindol-2-yl)-2-fluoro-5H-5-oxo-benzo[5.6]pyrano[2.3.4-ij]quinolizine-6-carboxylic acid;

1-(3-aminomethylpyrrolidiny)-2-fluoro-5H-5-oxo-benzo[5.6 ]pyrano[2.3.4-ij]quinolizine-6-carboxylic acid;

1-(3-(ethylaminomethyl)pyrrolidiny)-2-fluoro-5H-5-oxo-benzo[5.6]pyrano[2.3-4ij]quinolizine-6-carboxylic acid;

1-(3-(1-amino-1-methylethyl)pyrrolidinyl)-2-fluoro-5H-5-oxo-benzo[5.6]pyrano[2.3.4-ij]quinolizine-6-carboxylic acid;

1-(3-(1-aminoethyl)pyrrolidinyl)-2-fluoro-5H-5-oxo-benzo[5.6]pyrano[2.3.4ij]quinolizine-6-carboxylic acid;

1-(3-(1-aminocyclopropyl)pyrrolidinyl)-2-fluoro-5H-5-oxo-benzo[5.6]pyrano[2.3.4-ij]quinolizine-6-carboxylic acid;

1-(4-amino-2,3,3a,4,7,7a-hexahydro-[1H]-isoindol-2-yl)-2-fluoro-5H-5-oxo-benzo[5.6]pyrano[2.3.4-ij]quinolizine-6-carboxylic acid;

1-(4-amino-2,3,3a,4,5,7a-hexahydro-[1H]-isoindo-2-yl)-2-fluoro-5H-5-oxo-benzo[5.6]pyrano[2.3.4-ij]quinolizine-6-carboxylic acid;

1-(4-amino-2,3,4,5,6,7-hexahydro-[1H]-isoindol-2-yl)-2-fluoro-5H-5-oxo-benzo[5.6]pyrano[2.3.4-ij]quinolizine-6-carboxylic acid;

1-(3-amino-azetidinyl)-2-fluoro-5H-5-oxo-benzo[5.6]pyrano[2.3.4-ij]quinolizine-6-carboxylic acid;

1-(3-(norvalylamino)pyrrolidinyl)-2-fluoro-5H-5-oxo-benzo[5.6]pyrano[2.3.4-ij]quinolizine-6-carboxylic acid;

1-(3-(alanylamino)pyrrolidinyl)-2-fluoro-5H-5-oxo-benzo[5.6]pyrano[2.3.4-ij]quinolizine-6-carboxylic acid;

1-(6-amino-3-azabicyclo[3.1.0]hex-3-yl)-2-fluoro-5H-5-oxo-benzo[5.6]pyrano[2.3.4-ij]quinolizine-6-carboxylic acid;

1-(1-amino-5-azaspiro[2.4]hept-5-yl)-2-fluoro-5H-5-oxo-benzo[5.6]pyrano[2.3.4-ij]quinolizine-6-carboxylic acid;

1-(piperazinyl)-2-fluoro-5H-5-oxo-benzo[5.6]pyrano[2.3.4-ij]quinolizine-6-carboxyl acid;

1-(2-methylpiperazinyl)-2-fluoro-5H-5-oxo-benzo[5.6]pyrano[2.3.4-ij]quinolizine-6-carboxylic acid;

1-(4-methylpiperazinyl)-2-fluoro-5H-5-oxo-benzo[5.6]pyrano[2.3.4-ij]quinolizine-6-carboxylic acid;

1-(3-aminopiperidinyl)-2-fluoro-5H-5-oxo-benzo[5.6]pyrano[2.3.4-ij]quinolizine-6-carboxylic acid;

1-(4-aminopiperidinyl)-2-fluoro-5H-5-oxo-benzo[5.6]pyrano[2.3.4-ij]quinolizine-6-carboxylic acid;

1-(3-aminopyrrolidiny)-2-fluoro-5H-9-methyl-5-oxo-benzo[5.6]pyrano[2.3.4-ij]quinolizine-6-carboxylic acid;

1-(3-aminopyrrolidiny)-2-fluoro-5H-9-methoxy-5-oxo-benzo[5.6]pyrano[2.3.4-ij]quinolizine-6-carboxylic acid;

1-(3-aminopyrrolidiny)-2-fluoro-5H-9,11-dimethyl-5-oxo-benzo[5.6]pyrano[2.3.4-ij]quinolizine-6-carboxylic acid; or 1-(3-aminopyrrolidiny)-2-fluoro-5H-9,11-dimethoxy-5-oxo-benzo-[5.6]pyrano[2.3.4-ij]quinolizine-6-carboxylic acid.

5. A compound according to claim 3 which is:

1-(1-morpholinyl)-2-fluoro-5H-5-oxo-benzo[5.6 ]pyrano[2.3.4-ij]quinolizine-6-carboxylic acid;

1-(3-amino-pyrrolidinyl)-2-fluoro-5H-5-oxo-benzo[5.6]pyrano[2.3.4-ij]quinolizine-6-carboxylic acid; or 1-(3aα, 4β, 7aα-4-aminooctahydro-[1H]-isoindol-2-yl)-2-fluoro-5H-5-oxo-benzo[5.6]pyrano[2.3.4-ij]quinolizine-6-carboxylic acid.

6. A compound according to claim 1 wherein A is sulfur.

7. A compound according to claim 6 wherein $R^1$ is selected from the group consisting of amino, $C_1$–$C_6$-alkylamino, hydroxy-$C_1$–$C_6$-alkylamino, bicyclic nitrogen-containing heterocycle selected from the group consisting of benzopyrrolidine, octahydroisoindole, bicyclo[3.2.2]-nonane and azabicyclo[3.1.0]hex, nitrogen containing aromatic heterocycle selected from the group consisting of pyridine, pyrazine, pyrimidine, pyrrole, pyrazole, imidazole, thiazole, oxazole, isoxazole and nitrogen-containing heterocycle selected from the group consisting of azaspiro[2.4]hept, azetidine, pyrrolidine, piperidine, piperazine, morpholine, and thiomorpholine; $R^2$ is halo; and $R^4$ and $R^5$ are hydrogen.

8. A compound according to claim 7 which is:

1-(1-morpholinyl)-2-fluoro-5H-5-oxo-benzo[5.6]thiapyrano[2.3.4-ij]quinolizine-6-carboxylic acid; and 1-(3-amino-pyrrolidinyl)-2-fluoro-5H-5-oxo-benzo[5.6]thiapyrano[2.3.4-ij]quinolizine-6-carboxylic acid.

9. A compound according to claim 1 wherein A is oxygen or sulfur, and $R^1$ is selected from the group consisting of hydroxy, protected-hydroxy, $C_1$–$C_6$-alkoxy and halo.

10. A compound according to claim 9 which is 1-chloro-2-fluoro-5H-5-oxo-benzo[5.6]pyrano[2.3.4-ij]quinolizine-6-carboxylic acid;

1-hydroxy-2-fluoro-5H-5-oxo-benzo[5.6]pyrano[2.3.4-ij]quinolizine-6-carboxylic acid;

1-t-butyloxy-2-fluoro-5H-5-oxo-benzo[5.6]pyrano[2.3.4-ij]quinolizine-6-carboxylic acid;

1-chloro-2-fluoro-5H-5-oxo-benzo[5.6]thiopyrano[2.3.4-ij]quinolizine-6-carboxylic acid;

1-hydroxy-2-fluoro-5H-5-oxo-benzo[5.6]thiopyrano[2.3.4-ij]quinolizine-6-carboxylic acid; or 1-t-butyloxy-2-fluoro-5H-5-oxo-benzo[5.6]thiopyrano[2.3.4-ij]quinolizine-6-carboxylic acid.

11. A pharmaceutical composition for treating a bacterial or neoplastic infection comprising a therapeutically effective amount of a compound according to claim 3 and a pharmaceutically acceptable carrier.

12. A pharmaceutical composition for treating a bacterial or neoplastic infection comprising a therapeutically effective amount of a compound according to claim 5 and a pharmaceutically acceptable carrier.

13. A method of treating a bacterial or neoplastic infection in a human or other animal host, comprising administering to the host a therapeutically effective amount of a compound according to claim 3.

14. A method of treating a bacterial or neoplastic infection in a human or other animal host, comprising administering to the; host a therapeutically effective amount of a compound according to claim 5.

15. A pharmaceutical composition for treating a bacterial or neoplastic infection comprising a therapeutically effective amount of a compound according to claim 7 and a pharmaceutically acceptable carrier.

16. A method of treating a bacterial or neoplastic infection in a human or other animal host, comprising administering to the host a therapeutically effective amount of a compound according to claim 7.

* * * * *

UNITED STATES PATENT AND TRADEMARK OFFICE
CERTIFICATE OF CORRECTION

PATENT NO. : 5,618,813
DATED : April 8, 1997
INVENTOR(S) : Chu et al.

It is certified that error appears in the above-indentified patent and that said Letters Patent is hereby corrected as shown below:

Column 27, line 29, change "(3,2,2,7-nonane" to --[3,2,2,]-nonane--.

Column 27, line 34, change "azetidine" to --azaspiro [2.4]hept, azetidine--.

Column 27, line 48, change "hydroxy-.$C_1$-$C_6$-alkylamino" to --hydroxy-$C_1$-$C_6$-alkylamino--.

Column 28, line 40, change "carboxyl" to --carboxylic--.

Column 30, line 22, change "the;" to --the--.

Signed and Sealed this

Second Day of September, 1997

Attest:

BRUCE LEHMAN

Attesting Officer

Commissioner of Patents and Trademarks